(12) United States Patent
Soothill et al.

(10) Patent No.: US 7,807,149 B2
(45) Date of Patent: Oct. 5, 2010

(54) BACTERIOPHAGE-CONTAINING THERAPEUTIC AGENTS

(75) Inventors: James Soothill, London (GB); Catherine Hawkins, Southampton (GB); David Harper, Southampton (GB)

(73) Assignee: Biocontrol Limited, Southampton, Hampshire (GB)

( * ) Notice: Subject to any disclaimer, the term of this patent is extended or adjusted under 35 U.S.C. 154(b) by 968 days.

(21) Appl. No.: 10/565,347

(22) PCT Filed: Jul. 23, 2004

(86) PCT No.: PCT/GB2004/003237

§ 371 (c)(1), (2), (4) Date: Jul. 12, 2006

(87) PCT Pub. No.: WO2005/009451

PCT Pub. Date: Feb. 3, 2005

(65) Prior Publication Data

US 2007/0190033 A1      Aug. 16, 2007

(30) Foreign Application Priority Data

Jul. 23, 2003  (GB) ................... 0317240.0
May 14, 2004  (GB) ................... 0410855.1

(51) Int. Cl.
*A01N 63/00* (2006.01)
*A61K 39/38* (2006.01)
*A61K 39/40* (2006.01)
*A61K 39/108* (2006.01)

(52) U.S. Cl. ............... 424/93.6; 424/184.1; 424/170.1; 424/260.1; 424/93.47

(58) Field of Classification Search .............. None
See application file for complete search history.

(56) References Cited

U.S. PATENT DOCUMENTS

| 4,828,999 | A  | 5/1989  | Jackson         |
|-----------|----|---------|-----------------|
| 6,461,608 | B1 | 10/2002 | Averback et al. |
| 2002/0001590 | A1 | 1/2002 | Kelly et al.  |
| 2002/0090356 | A1 | 7/2002 | Waddell et al.|

FOREIGN PATENT DOCUMENTS

| WO | WO-97/39111   | 10/1997 |
| WO | WO-98/47521   | 10/1998 |
| WO | WO-01/50866   | 7/2001  |
| WO | WO-02/07742   | 1/2002  |
| WO | WO-2004/062677| 7/2004  |

OTHER PUBLICATIONS

Slopek et al. (Archivum Immunologiae Et Therapiae Experimentals, 1984; 32(3): 317-35).*
Carlton, Archivum Immunologiae Et Therapiae Experimentalis (1999) 47(5):267-274.
Database WPI Accession No. 1990-021061, Class B04 and SU 1 472 500, Apr. 15, 1989.
Database WPI Accession No. 2002-689103, and RU 2186574, Jan. 24, 2001.
Hanlon et al., Applied and Environmental Microbiology (2001) 67(6):2746-2753.
International Search Report for PCT/GB2004/003237, mailed on Nov. 8, 2004, 6 pages.
Kudva et al., Appl. Environ. Biol. (1999) 65:3767-3773.
Soothill, Burns (1994) 20(3):209-211.
Tait et al., Biofouling (2002) 18(4):305-311.
UK Search Report for GB 0317240.0 dated Oct. 15, 2003.

* cited by examiner

*Primary Examiner*—Robert B Mondesi
*Assistant Examiner*—Lakia J Tongue
(74) *Attorney, Agent, or Firm*—Evan Law Group LLC

(57) ABSTRACT

The present invention relates in its broadest aspect to combined phage/antibiotic therapy. More particularly, it relates to use of (i) one or more bacteriophages and (ii) one or more antibiotics in the manufacture of a combined product for simultaneous, separate or sequential administration of (i) and (ii) to treat a bacterial infection characterized by biofilm formation, for example an infection comprising or consisting of *P. aeruginosa*. Treatment in this context may be either therapeutic or prophylactic treatment. Also provided are deposited bacteriophages each exhibiting different strain specificity against *P. aeruginosa* and combinations of such bacteriophages, e.g. a panel of six deposited bacteriophages which was found to be effective against a high percentage of clinical isolates of *P. aeruginosa* from canine ear infections.

7 Claims, 6 Drawing Sheets

BACTERIOPHAGE-CONTAINING THERAPEUTIC AGENTS

CROSS-REFERENCE TO RELATED APPLICATIONS

This application is the national phase of PCT application PCT/GB2004/003237 having an international filing date of Jul. 23, 2004, which claims priority from United Kingdom application number GB 0317240.0, filed Jul. 23, 2003 and United Kingdom application number GB 0410855.1, filed May 14, 2004. The contents of these documents are incorporated herein by reference.

FIELD OF THE INVENTION

The present invention relates to therapeutic and diagnostic preparations comprising viruses that kill bacteria (bacteriophages). In particular, the invention provides in a preferred aspect therapeutic compositions comprising combinations of bacteriophages as control agents for infections of animals and humans caused by pathogenic bacteria of the species *Pseudomonas aeruginosa*. The invention also relates to use of bacteriophages in combination with antibiotics to treat bacterial infections characterised by biofilm formation, especially for example such infections comprising infection with *Pseudomonas aeruginosa* such as canine ear infections

BACKGROUND TO THE INVENTION

Antibiotics have been seen for many years as "the answer" to the problem of bacterial infections. This attitude persisted until the development of the wide-ranging (and in some cases total) resistance to antibiotics seen within the last ten years. In many cases it is necessary to use expensive "drugs of last resort" (such as vancomycin for *Staphylococcus aureus*), which often require complex routes of administration and show toxic side effects, necessitating prolonged hospital treatment.

Even to these drugs, resistance is reaching worrying levels. It is now clear that bacteria can adapt to resist any antibiotic. Even the new generation drugs such as linezolid are already generating resistance [Mutnick et al (2003) An. Pharmacother. 37:769-774; Rahim et al (2003) Clin Infect Dis 36: E146-148], and it is clear from recent developments that resistance develops faster than new antibiotics can be produced, evaluated and processed through regulatory approvals.

A further disadvantage of antibiotic treatment is its lack of specificity. Antibiotics can kill a wide range of bacteria and this can lead to recolonisation of the body by inappropriate and often harmful bacteria. There is therefore need for antibacterial treatments that show specificity against particular bacterial species so that little resistance is induced in the normal flora.

The need for new forms of antibacterial therapy is well illustrated by the case of infection with the gram-negative aerobic bacterium *Pseudomonas aeruginosa*.

*Pseudomonas aeruginosa* is a serious opportunistic bacterial pathogen. Infections caused by *Pseudomonas aeruginosa* include:
- Otitis externa and otitis media in dogs, ear infections which exemplify biofilm-based colonization of a body surface and which are common in inbred (pedigree) dogs;
- Otitis externa of humans ("swimmers ear") along with other ear infections and other topical infections of humans including *Pseudomonas keratitis* and *Pseudomonas folliculitis*;
- Infection of burns and skin grafts in humans;
- Hospital-acquired infections;
- Lung infection in cystic fibrosis (CF) patients.

0-15% of nosocomial (hospital acquired) infections are due to *Pseudomonas aeruginosa*, with 2 million cases annually in the US alone. In some situations, the frequency is even higher. Of around 150,000 burn patients treated in US hospitals and burn centres per year, 26% have *Pseudomonas aeruginosa* infections. *Pseudomonas aeruginosa* is notorious for its resistance to antibiotics so infections caused by it can be difficult to treat. One of its natural habitats is soil, where it is exposed to organisms that produce antibiotics. This may well have led to the development of resistance mechanisms coded for both by genes on the chromosome and by transferable genetic elements known as plasmids. The properties of the *P. aeruginosa* outer membrane are important in conferring resistance. An additional resistance mechanism is its tendency to grow on available surfaces as complex layers known as biofilms [Donlan (2002) Emerging Infectious Diseases 8: 881-890; Fletcher & Decho (2001) Biofilms in Encyclopaedia of Life Sciences, Nature Publishing, London;] that are resistant to far higher concentrations of antibiotics than are required to kill individual cells [Chen et al (2002) Pseudomonas infection; Qarah et al (2001) *Pseudomonas aeruginosa* infections; Todar K. (2002) Todar's Online Textbook of Bacteriology: *Pseudomonas aeruginosa*; Iglewski B. H (1996) *Pseudomonas*. Medical Microbiology 4th edition, S. Baron (ed.). University of Texas]. The practical effect of this is demonstrated by infections in cystic fibrosis patients, virtually all of whom eventually become infected with a bacterial strain that cannot be eradicated by the use of antibiotics, even when the isolated strain may appear to be sensitive in the laboratory [Hoiby N (1998) *Pseudomonas* in cystic fibrosis: past, present, future. European Cystic Fibrosis Society Joseph Levy Memorial Lecture].

*Pseudomonas aeruginosa* expresses a range of genes (most notably the algC gene) which produce the extracellular components responsible for biofilm formation, which are often polysaccharide in nature (Friedman and Kolter, Mol. Microbiol. (2004) 3, 675-690). Such biofilm formation is now known to be a characteristic of many important pathogenic bacteria contributing to increased resistance to antibiotics. Such biofilms may comprise more than one type of bacterium supported and surrounded by an excreted extracellular matrix and assist bacteria to colonise surfaces from marine reefs to teeth enamel. Biofilms allow bacteria to attach to surfaces and to attain population densities which would otherwise be unsupportable. They impart increased resistance to not only antibiotics but many environmental stresses including toxins such as heavy metals, bleaches and other cleaning agents. It was previously thought that contribution of biofilm formation to antibiotic resistance was primarily a physical process arising from limitation of diffusion, but more recent evidence has shown that some biofilms appear to have specific abilities to trap antibiotics (Mah et al., Nature (2003) 426, 306-310). It is known that bacteria within biofilms can be 100 to 1000 times more resistant to antibiotics than the same strain of bacteria growing in single-celled ("planktonic") forms. This increased resistance means that bacteria that are apparently sensitive to antibiotics in a laboratory test may be resistant to therapy in a clinical setting. Even if some are cleared, biofilms may provide resistant reservoirs permitting rapid colonisation once antibiotics are no longer present. It is clear therefore that biofilms are major factors in many human diseases.

Chemical treatments are unsuited to use against biofilms since this is precisely what they have evolved to counter and many surfaces where biofilms aid bacterial pathogenesis are poorly suited to rigorous abrasion. Physical abrasion does provide a means to disrupt biofilms. However, many surfaces where biofilms aid bacterial pathogenesis are poorly suited to rigorous abrasion. For example, the surfaces of wounds or burns are extremely sensitive and delicate. Even where abrasion is both suitable and in routine use, clearing of biofilms is limited. Oral plaque on the surface of teeth is a biofilm and is partially cleared by regular brushing. However, bacteria are maintained on unbrushed surfaces (for example in the gaps between teeth) and can recolonise cleared surfaces both rapidly and effectively. From this, it is clear that existing approaches to clearing biofilms are of limited efficacy.

In addition to the biofilm problem, only a few antibiotics in any case are capable of effective action against *Pseudomonas aeruginosa*, including fluoroquinolones, gentamicin and imipenem, and even these antibiotics are not effective against all strains. Multidrug resistance is common and increasing [Friedland I et al (2003). Diagnostic Microbiology and Infectious Disease 45:245-50; Henwood et al (2001). Journal of Antimicrobial Chemotherapy 47: 789-799]. The U.S. National Nosocomial Infections Surveillance System Report of June 1999 [Gerberding J et al (2001). National Nosocomial Infections Surveillance (NNIS) System Report, data summary from January 1992-June 2001, issued August 2001. U.S. Department of Health and Human Services, Atlanta] states that antibiotic resistance of *Pseudomonas aeruginosa* isolated from nosocomial infections in ICU patients in 1999 had increased over the 1994-98 period for all classes of antibiotics studied. There is therefore a demonstrated need for new approaches to the control of *Pseudomonas aeruginosa* infection. The inventors in this instance have addressed this problem through use of new bacteriophage-based therapies.

Bacteriophages (often known simply as "phages") are viruses that grow within bacteria. The name translates as "eaters of bacteria" and reflects the fact that as they grow most bacteriophages kill the bacterial host as the next generation of bacteriophages is released. Early work with bacteriophages was hindered by many factors, one of which was the widespread belief that there was only one type of bacteriophage, a non-specific virus that killed all bacteria. In fact, the host range of bacteriophages (the spectrum of bacteria they are capable of infecting) is often very specific. This specificity may be considered a therapeutic strength as populations of bacteriophages can be selected to specifically eliminate only the target bacteria. Antibiotics, on the other hand, kill a wide range of bacteria and their use can consequently lead to disruption of the normal flora, leading to recolonisation of the body by inappropriate and often harmful bacteria.

Despite the therapeutic advantages afforded by the host specificity of bacteriophages, this characteristic has the disadvantage that it can be difficult to achieve breadth of coverage of target strains. For this reason, there has been interest in finding combinations of bacteriophages having broad targeting capability in relation to particular types of bacterial infection (see for example Pirsi, The Lancet (2000) 355,1418)

The inventors in this instance have established a combination of bacteriophages consisting of six bacteriophages each with a different strain specificity against *Pseudomonas aeruginosa* and which is particularly suitable for broad targeting of *P. aeruginosa* infections, especially, for example, canine ear infections. The combination was found to be capable of destroying 90% of *P. aeruginosa* strains sampled from canine otitis externa and other canine ear infections. Furthermore, they have established that such a phage combination may be employed synergistically with antibiotic treatment to gain improved efficacy. As a consequence, it is now extrapolated that combined phage/antibiotic therapy represents a new general advantageous approach for tackling bacterial infections characterised by biofilm formation.

Phage and antibiotic therapy have previously been used together in Eastern Europe (see for example Bradbury, The Lancet (February 2004) 363, 624-625), but there was no specific relation to biofilm formation. Additionally, there have been suggestions that antibiotics can have adverse effect on use of bacteriophage therapy since bacteriophages use bacterial metabolism to replicate and this is inhibited by antibiotics (Payne and Janssen, Clinical Pharmacokinetics (2002) 42, 315-325).

SUMMARY OF THE INVENTION

In one aspect, the present invention thus provides the use of (i) one or more bacteriophages and (ii) one or more antibiotics in the manufacture of a combined product for simultaneous, separate or sequential administration of (i) and (ii) to treat a bacterial infection characterized by biofilm formation, e.g. a bacterial infection comprising or consisting of *Pseudomonas aeruginosa*.

Treatment of such a bacterial infection in this context will be understood to mean either therapeutic treatment or prophylactic treatment. Bacteriophages are uniquely suited to prophylactic use because:

Chemical agents must be used above specific minimum levels if they are to be effective. Lower levels are at best ineffective. At worst, they can encourage the development of resistance.

Replicating biological agents in contrast have the innate ability to generate therapeutic dose as and when needed, even from a very low input dose The present invention also provides a panel of bacteriophages active against *Pseudomonas aeruginosa* each exhibiting a different strain specificity. More particularly, the invention provides eight bacteriophages deposited at the National Collection of Industrial and Marine Bacteria, Aberdeen, U.K. on 24th Jun. 2003 as NCIMB 41174, NCIMB 41175, NCIMB 41176, NCIMB 41177, NCIMB 41178, NCIMB 41179, NCIMB 41180 and NCIMB 41181 and mutants thereof which retain the ability to target *P. aeruginosa*. While members of the panel might be used individually, use of combinations of such phages is preferred so as to broaden target strain efficacy. As indicated above, a combination of six of these phages, more particularly N41174 to N41179, has been found to be particularly advantageous in treating canine ear infections comprising *P. aeruginosa* and might also be advantageously employed in treating other *P. aeruginosa* infections, especially in combination with antibiotic treatment. Such phage treatment or combined phage and antibiotic treatment may also be combined with use of alginase. Again, such treatment will be understood to encompass prophylactic treatment.

The invention also extends to non-therapeutic methods of removing, reducing or preventing bacterial contamination characterised by biofilm formation. In one embodiment, such a method comprises applying to the site or prospective site of contamination one or more bacteriophages capable of targeting bacteria of the contamination and simultaneously, separately or sequentially thereto one or more antibiotics or antiseptics. In another embodiment, there is provided a method of removing, reducing or preventing bacterial contamination comprising or consisting of *P. aeruginosa* which comprises applying to the site or prospective site of contamination one or more of the deposited bacteriophages noted above.

The phages of the invention may also be used in methods for detecting the presence of target *P. aeruginosa* strains. Accordingly, the invention provides a method of detecting *P. aeruginosa* in an in vitro sample, e.g. a biological sample from a human or animal for diagnostic purpose, comprising contacting said sample with one or more bacteriophages of the invention, and determining whether said bacteriophage(s) are capable of killing bacteria in said sample.

The invention also provides a method of identifying a bacterial strain indicative for a bacteriophage selected from the eight deposited bacteriophages listed above, the method comprising the steps of measuring plaque formation by the bacteriophage in a number of bacterial strains and selecting a strain which allows at least 1000 times more plaque formation by said bacteriophage than by any other of said deposited bacteriophages.

Also provided are bacterial strains identified by such a method that can be used to identify bacteriophages present in preparations intended for therapeutic use and/or to identify strains present in tissue samples obtained during such therapeutic use or following such use. Such bacterial strains may also be used as count strains to determine the amount of a particular bacteriophage capable of infecting the strain in a bacteriophage preparation.

BRIEF DESCRIPTION OF THE FIGURES

FIG. 1: Efficacy of bacteriophages against different strains of *Pseudomonas aeruginosa*. Strains named in bold were resistant.

☐ Plaques observed

▨ No plaques

|X| Either (1) Some dilutable inhibition observed but no obvious plaques, or (2) by visual assessment *P. aeruginosa* isolate deemed poorly susceptible

|ND| Not Done

The six bacteriophages BC-BP-01, BC-BP-02, BC-BP-03, BC-BP-04, BC-BP-05, and BC-BP-06 (corresponding to deposits NCIMB 41174, NCIMB 41175, NCIMB 41176, NCIMB 41177, NCIMB 41178 and NCIMB 41179 respectively) together resulted in 90% coverage of all screened *P. aeruginosa* strains.

Figure 2:
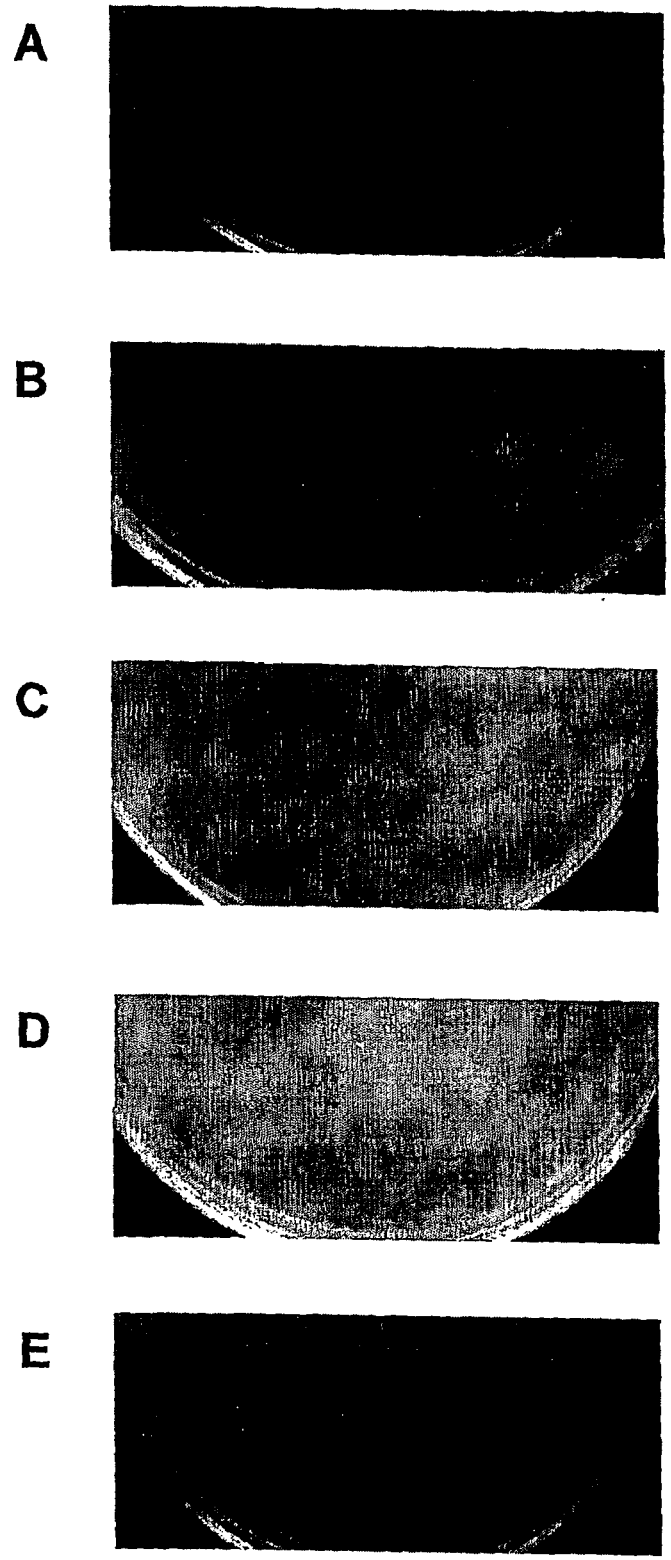

Examples of Bacterial Isolates used:

FIG. 2: Identification of a BC-BP-03 count strain. Plates of count strain infected as follows:
A: Uninfected.
B: Infected with BC-BP-03 (1,000,000-fold dilution).
C: Infected with BC-BP-01 (10-fold dilution).
D: Infected with BC-BP-04 (10-fold dilution).
E: Infected with BC-BP-02 (10 fold dilution).

Figure 3:
Figure 3:

FIG. 3: Resolution of infection in a dog ear treated with bacteriophage BC-BP-04:
A: Appearance of right ear 24 hours after treatment with 400 infectious units of BC-BP-04.
B: Appearance of left ear which did not receive bacteriophage treatment.

Figure 4:
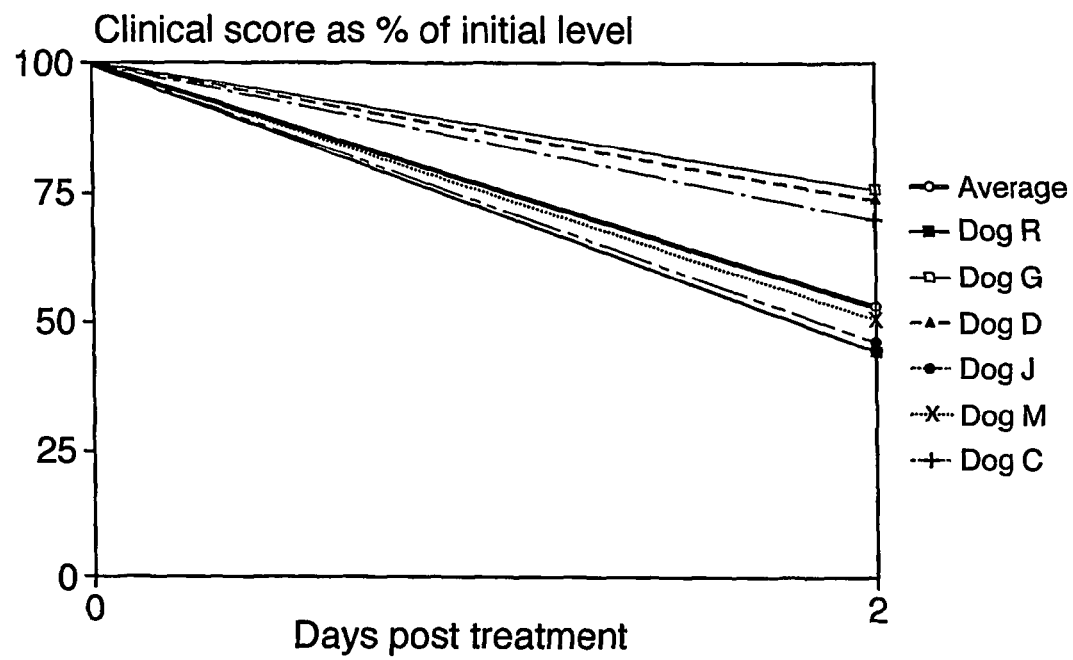

FIG. 4: Improvement in total clinical score as % of initial level (occlusion, erythema, ulceration, discharge type, discharge volume, odour) of six dogs with antibiotic resistant otitis after 2 days treatment with a combined bacteriophage preparation containing the six bacteriophages NCIMB 41174 to NCIMB 41179 (BioVet-PA) (thicker continuous line is average)

Figure 5:
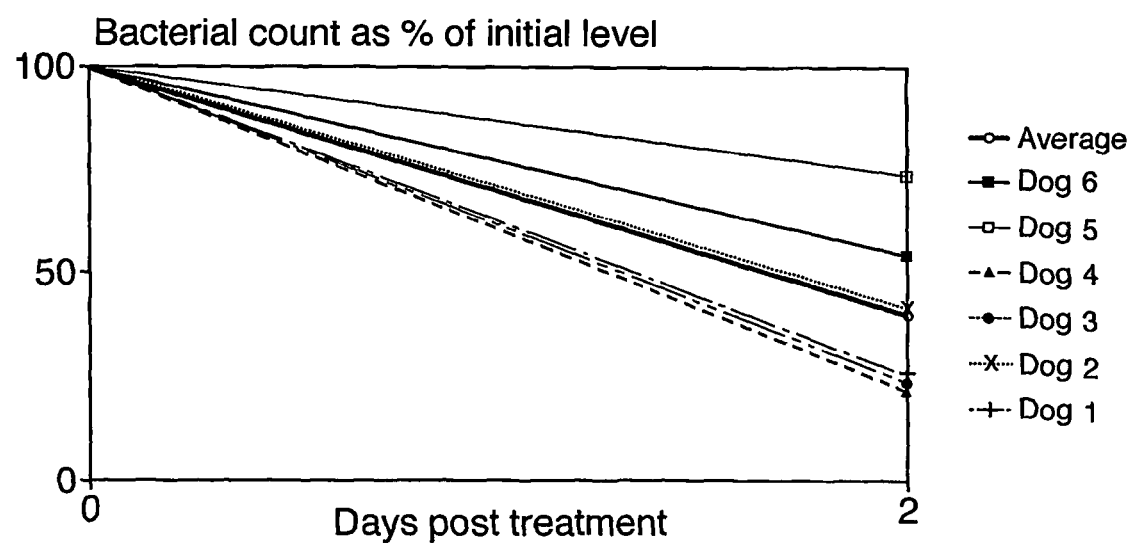

FIG. 5: *Pseudomonas* bacteria count per gramme of detritus as % of initial level in the same dog treatment group after 2 days treatment (thicker continuous line is average)

Figure 6:
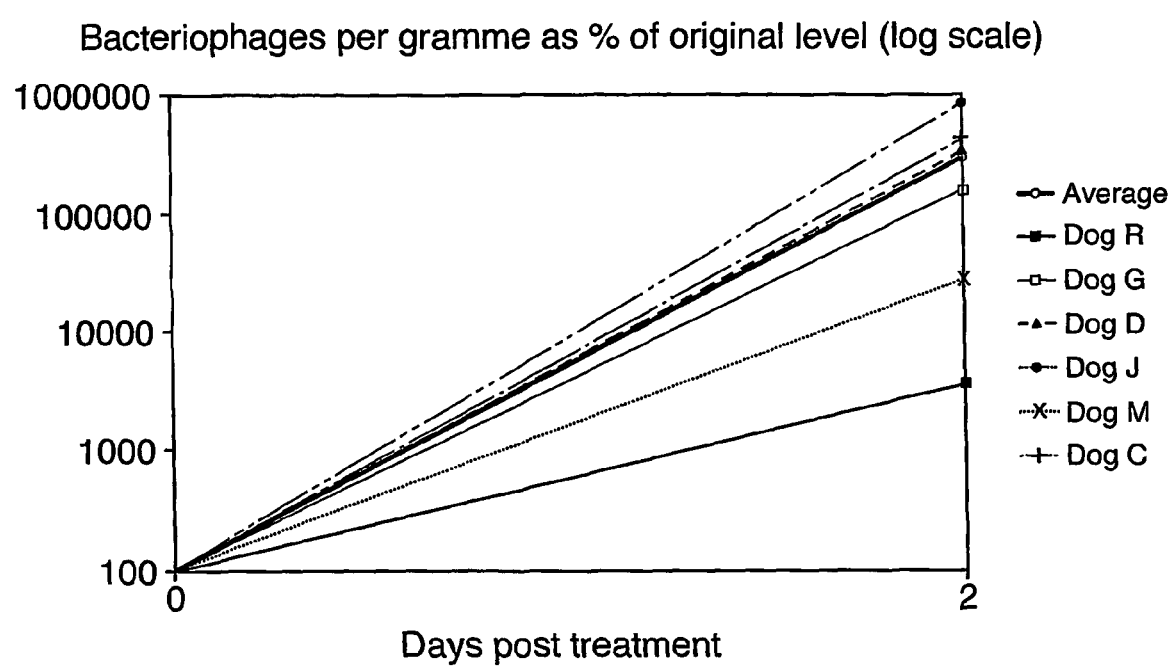

FIG. 6: Number of bacteriophages per gramme of detritus as % of original level (log scale) in the same dog treatment group after 2 days of treatment (thicker continuous line is average)

DETAILED DESCRIPTION OF THE INVENTION

The present invention utilises panels of naturally-occurring viruses that infect pathogenic bacteria. Such panels can be formulated into therapeutic medicaments suitable for evaluation through the clinical trials process. As indicated above, in one aspect, the invention provides use of (i) one or more bacteriophages and (ii) one or more antibiotics in the manufacture of a combined product for simultaneous, separate or sequential administration of (i) and (ii) to treat a bacterial infection characterised by biofilm formation. For this purpose, a panel of two or more bacteriophages may be employed in the manufacture of a single combined bacteriophage preparation. The bacteriophages of the chosen panel will preferably be capable of infecting the same bacterial species and each exhibit different strain specificity.

| Bacteria | Strain | Species origin | Date isolated | Location | Number of passages |
|---|---|---|---|---|---|
| 7 Used for BC-BP-04 | *Pseudomonas aeruginosa* | Human | 1960's | U.S. army surgical research unit Ft Sam Houston, Texas, U.S.A | 10-100 |
| 3708 Used for BC-BP-01 | *Pseudomonas aeruginosa* | Human | 1970's | Public Health Laboratory, Cambridge, U.K | 10-100 |
| G184 Used for BC-BP-02 | *Pseudomonas aeruginosa* | Human | 1980's | Edinburgh, U.K | 10-100 |
| 919686 Used for BC-BP-05 | *Pseudomonas aeruginosa* | Dog | 1980's | Idexx Laboratories, Wetherby, U.K | 2-3 |
| 27225 Used for BC-BP-06 | *Pseudomonas aeruginosa* | Dog | 2003 | Royal Veterinary College, London, U.K | 2-3 |
| C33138 Used for BC-BP-03 | *Pseudomonas aeruginosa* | Dog | 2003 | Axiom laboratories, Devon, U.K | 2-3 |

The antibiotics of use may belong to any class known to be active against any of the bacterial species known or thought likely to be present in the biofilm. Preferably, the one or more antibiotics will be administered after the one or more bacteriophages such that bacteriophage replication has become established before any antibiotic treatment begins. In this case, antibiotic treatment may be delayed up to days from application of the one or more bacteriophages, e.g. from 1 to 2, 3, 4, 5, 6, 7, 8, 9 or 10 days. Preferably, a sample will be taken from the infection site to check that bacteriophage replication is occurring before antibiotic treatment begins. Where a panel of bacteriophages is employed with each member of the panel exhibiting different strain specificity, it will suffice that at least a proportion of the panel can target the bacterial infection. This may be a single bacteriophage or more than one bacteriophage.

Where a panel of bacteriophages is employed, the bacteriophages may be provided in the form of a single therapeutic composition or as a number of separate compositions each comprising one or more members of the panel. A suitable panel may consist of two or more, three or more, four or more, five or more, or six or more bacteriophage strains. Such a panel may comprise two, three, four, five, six, seven, eight, nine, ten, fifteen, twenty or more different bacteriophages. The bacteriophages may be from the same or different taxonomical groups of viruses.

Bacteriophages with the potential to control bacterial infections may be identified by a process of bioprospecting. This involves the identification of such agents by assay of material from sources rich in the target bacteria, and introduction of such material to cultures of the target bacteria. A suitable sample may be taken from sewage from a hospital, urban or other source.

Typically, sewage samples are mixed with powdered or liquid bacterial growth media and with the target strains of bacteria against which it is desired to isolate specific bacteriophages.

Samples are screened for the presence of suitable bacteriophages by monitoring their effect on bacterial cells. Typically this may involve determining bacterial death by observing the formation of cleared zones in bacteria grown on solid substrates ("plaques") or a loss of turbidity in liquid culture.

Each of the bacteriophage strains selected for formation of a panel for use in combined phage and antibiotic therapy as discussed above will typically have activity against the same target bacterial species. By activity is meant the ability of a bacteriophage to infect that bacterial species and to have a detrimental effect on the infected cells. This may be seen in the death of some or all of the infected cells. Preferably the bacteriophages will have activity against the target bacterial species, but will have no activity or lower activity against other bacterial species.

Once isolated, bacteriophages may be assayed against multiple strains (isolates) of the target bacterial species in order to determine their activity and specificity. These isolates may be taken from patients either infected or colonised with a bacterial species. Suitable isolates may also be obtained from natural or environmental sources of the bacterial target strain, such as soil samples. Methods of isolating bacteria from such samples are well known in the art. For example, suitable *P. aeruginosa* isolates for testing of bacteriophage panels may be obtained from known *P. aeruginosa* infections such as otitis externa, topical infections, burn infections, nosocomial infections, or other infections. Suitable isolates may also be obtained from natural sources of *P. aeruginosa*, such as soil samples.

As indicated above, it is particularly desirable to put together a phage panel which exhibits a broader strain specificity for the target bacterial species than any of the individual selected phages. That is, the panel of bacteriophages is able to kill a greater number of strains or isolates of the target bacterial species than any of the individual selected bacteriophages.

Figures 1A, 1B:
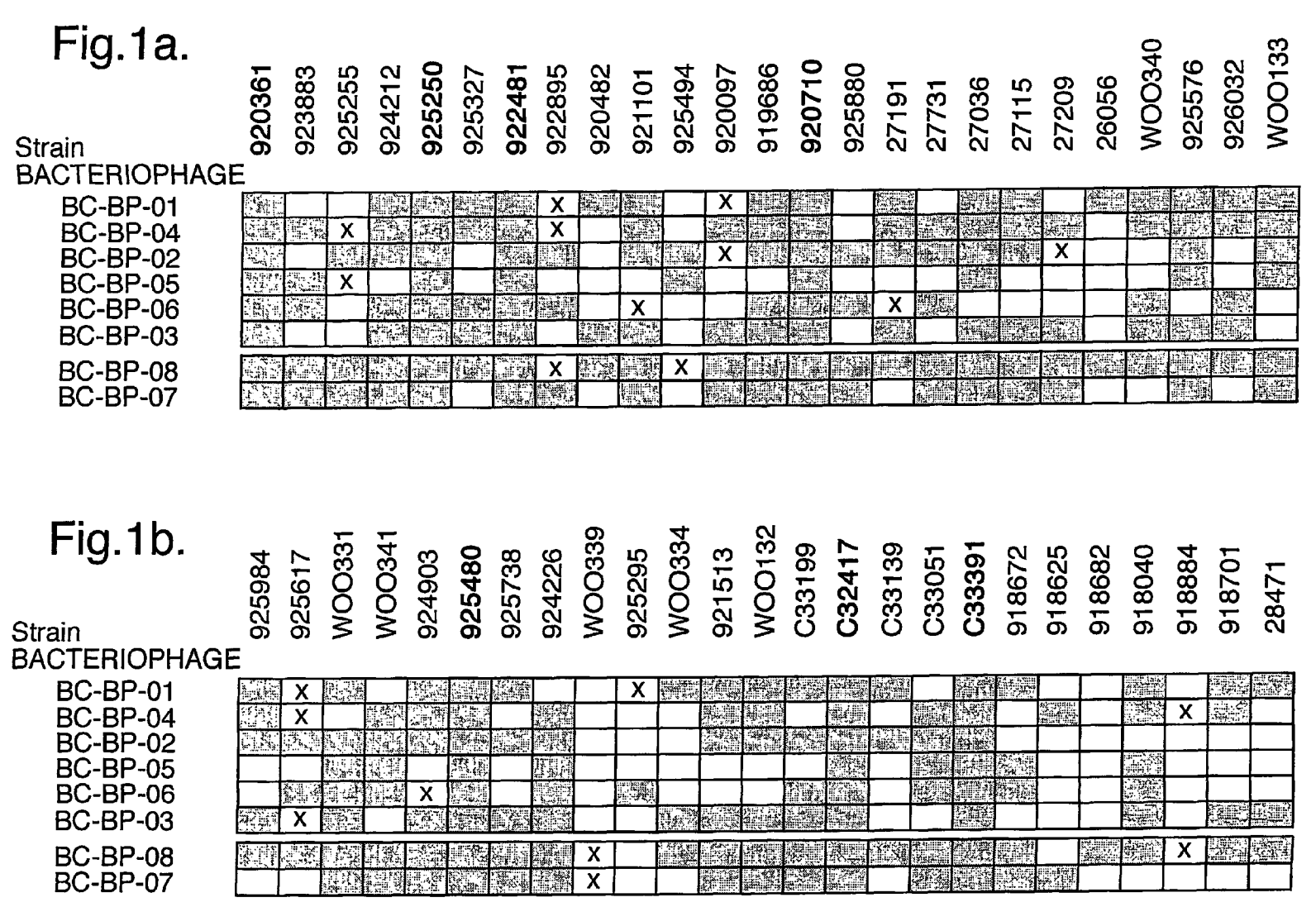
Figures 1C, 1D:
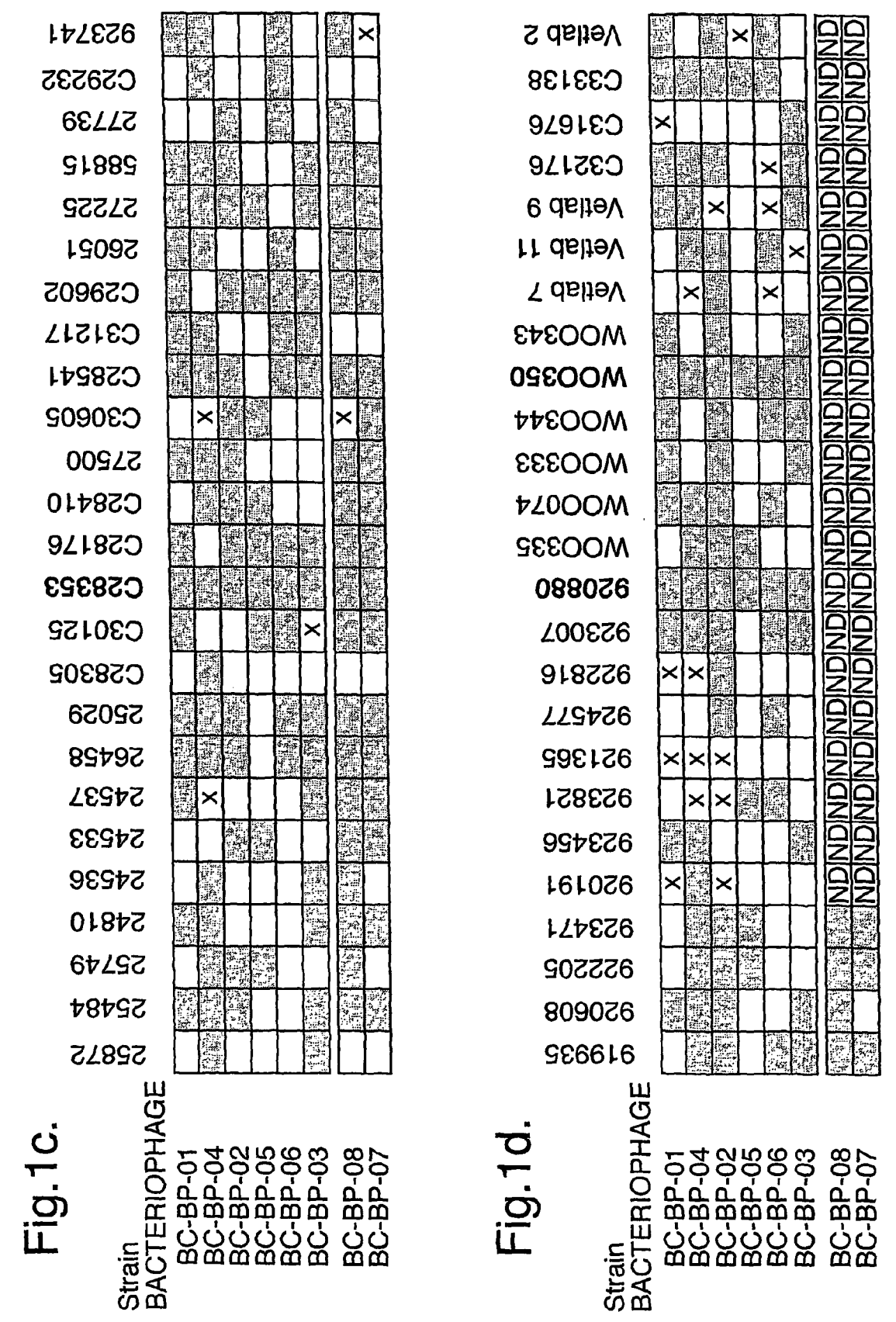

This may be achieved by including in the preparation a number of bacteriophage strains each having different specificities for the target bacterial isolates giving the preparation an overall total effectiveness against many more strains than any of the individual bacteriophages. The phage panel may include one or more bacteriophage strains which are effective against a broad spectrum of bacterial isolates of the target species so that the bacteriophages in the preparation have overlapping effectiveness, with some specific isolates being targeted by multiple bacteriophages, thus helping to minimise any development of resistance. Individual strains of the target bacterial species may therefore be killed by one or more of bacteriophages making up a preparation. The activity of bacteriophages against a range of isolates, for example at least 50 isolates, may be tested and the resulting information correlated to identify a group of at least two different bacteriophages which have a combined effectiveness against the target bacterial species that is greater than the effectiveness of any of the individual bacteriophages. Such development of a panel is exemplified by the development of a panel of bacteriophages effective against *Pseudomonas aeruginosa* as shown in FIG. 1.

Bacteriophages may be grown separately in strains (growth strains) of the host (or a related species) that support growth to high levels, titrated and combined at therapeutic concentrations. Typically, this may range from 100 to 100,000,000 infectious units per dose for each bacteriophage in the mixture.

The amount of each bacteriophage employed will depend upon its virulence against the target bacterial species. Count bacterial strains may be used in the development of a panel, i.e. bacterial strains which are indicators for individual prospective members of the panel. A count strain may permit at least 1000 times more plaque formation by one prospective member of the phage panel than any other. In this way, a panel that is consistently effective against a wide range of bacterial isolates may be achieved.

As indicated above, combined phage/antibiotic therapy according to the invention may be particularly useful for example in targeting bacterial infection comprising or consisting of *Pseudomonas aeruginosa*. Such infection may be, for example, at the site of a skin burn or other skin wound. It may be in the lung, an ocular infection or an ear infection. In this context, such an infection comprising *P. aeruginosa* will be understood to include an infection consisting essentially of *P. aeruginosa*. Thus, phage therapy according to the invention may be applied to an infection composed entirely, predominantly or significantly of *P. aeruginosa*.

As previously noted above, the present invention provides eight deposited bacteriophage strains that are shown herein to be effective at killing a broad range of *P. aeruginosa* isolates, and mutants thereof which retain the ability to target the same bacterial species. The relevant bacteriophage strains which were deposited at the National Collection of Industrial and Marine Bacteria (23 St Machar Drive, Aberdeen, AB24 3RY, Scotland, UK) on 24 Jun. 2003 are as follows:

| Reference | NCIMB Deposit Number |
| --- | --- |
| BC-BP-01 | NCIMB 41174 |
| BC-BP-02 | NCIMB 41175 |
| BC-BP-03 | NCIMB 41176 |
| BC-BP-04 | NCIMB 41177 |
| BC-BP-05 | NCIMB 41178 |
| BC-BP-06 | NCIMB 41179 |
| BC-BP-07 | NCIMB 41180 |
| BC-BP-08 | NCIMB 41181 |

These bacteriophages may be employed therapeutically individually or as part of a phage panel to combat *P. aeruginosa* infection. For example, a phage panel for use in accordance with the invention may comprise any two, three, four, five, six, or seven or all eight of the deposited strains. Any of said deposited strains may be substituted by a mutant thereof which exhibits desired *P. aeruginosa* strain specificity. As indicated above, a panel consisting of the six strains BC-BP-01, BC-BP-02, BC-BP-03, BC-BP-04, BC-BP-05 and BC-BP-06 has been found to be particularly favourable, for example, for veterinary use to target canine ear infection either alone or more preferably in combination with antibiotic therapy. However, utility of this phage panel is not confined to such use. It may find use in targeting *P. aeruginosa* infection in a variety of clinical situations.

In a further aspect, the invention provides a pharmaceutical composition comprising one or more bacteriophages selected from the eight deposited bacteriophage strains noted above and mutants thereof which retain the ability to target *P. aeruginosa*, together with a pharmaceutical carrier or diluent carrier.

Suitable carriers and diluents include isotonic saline solutions, for example phosphate-buffered saline. The composition may be formulated for parenteral, intramuscular, intravenous, subcutaneous, transdermal, ocular or aural administration, e.g. a liquid formulation for administration as eye or ear drops. Such a bacteriophage preparation may be used directly, stored frozen in aqueous or other solution with an appropriate cryoprotectant (e.g. 10% sucrose), freeze dried and rehydrated prior to use, or rendered stable in some other formulation including (but not limited to) tablet, emulsion, ointment, or impregnated wound dressing or other item.

In a still further aspect, there is provided a combined product for simultaneous, separate or sequential administration of a panel of bacteriophages to treat a bacterial infection comprising or consisting of *P. aeruginosa*, each member of said panel having a different strain specificity and wherein said panel consists of two or more bacteriophages selected from NCIMB 41174, NCIMB 41175, NCIMB 41176, NCIMB 411177, NCIMB 41178, NCIMB 41179, NCIMB 41180 and NCIMB 41181 and mutants thereof which retain the ability to target *P. aeruginosa*. As indicated above, in an exemplified embodiment, the panel consists of the six bacteriophages NCIMB 41174 to NCIMB 41179. These may be employed individually or more preferably in a single pharmaceutical composition. A combined product or composition comprising one or more of the above-noted deposited bacteriophages may further comprise one or more antibiotics for simultaneous, separate or sequential administration to the one or more bacteriophages. Such a combined product or composition may alternatively or additionally comprise an alginase. The alginase may also be provided for simultaneous, separate or sequential administration to the selected one or more bacteriophages.

The target specificity of a bacteriophage may be altered by the choice of substrate on which it is grown. That is, two genetically identical bacteriophages may exhibit different target specificity when they have been grown on different substrates. In this case, a bacteriophage may be identified by the nucleotide sequence of its genome. A bacteriophage having the same genomic sequence as one of the eight deposited bacteriophage strains listed above is considered to be the same bacteriophage, even if the target specificity that it exhibits is not identical to that of the deposited strain.

As noted above, the invention also extends to mutants of the deposited strains which retain the ability to kill bacteria of the target species. In particular, the invention extends to mutant forms of these strains which retain similar or improved target specificity as the strain from which they are derived. Thus, one or more bacteriophages in a composition or combined product of the invention may be mutants derived from these deposited strains which retain the ability to infect and show activity against *Pseudomonas aeruginosa*.

Suitable mutant bacteriophages may be derived from any one of the eight deposited strains BC-BP-01, BC-BP-02, BC-BP-03, BC-BP-04, BC-BP-05, BC-BP-06, BC-BP-07 and BC-BP-08. A suitable mutant strain may retain the same target specificity as the strain from which it is derived. That is, it may infect and kill the same isolates or strains of the target bacterial species as the deposited bacteriophage. Similarly, it may be ineffective against the same bacterial isolates or strains as the deposited bacteriophage. Alternatively, mutant bacteriophage strains may be used which have altered target specificity, being more or less able to infect and kill particular isolates or strains of the bacterial target species.

Suitable mutant bacteriophage strains may have a similar genome to a deposited strain. That is, the nucleotide sequence of the genome of a mutant bacteriophage may retain sequence identity to the genome of the deposited bacteriophage from which it is derived. Suitable mutant strains may retain at least 90%, at least 95%, at least 97%, at least 98% or at least 99% nucleotide sequence identity to the genome of a deposited strain, across the whole length of the genome. Alternatively, these levels of sequence identity may be retained across only a part of the genome, for example those parts of the genome required for target specificity. In one embodiment, the genome of a mutant bacteriophage may comprise a gene encoding a further therapeutic protein, as explained below. In such a case, the bacteriophage genome may consist of a genome having a degree of nucleotide sequence identity as set out above, plus those sequences necessary for the expression of the additional therapeutic protein.

The UWGCG Package provides the BESTFIT program which can be used to calculate sequence identity (for example used on its default settings) (Devereux et al (1984) Nucleic Acids Research 12, 387-395). The PILEUP and BLAST algorithms can alternatively be used to calculate identity or line up sequences (typically on their default settings), for example as described in Altschul S. F. (1993) J Mol Evol 36:290-300; Altschul, S. F. et al (1990) J Mol Biol 215:403-10. Identity may therefore be calculated using the UWGCG package, using the BESTFIT program on its default settings. Alternatively, sequence identity can be calculated using the PILEUP or BLAST algorithms. BLAST may be used on its default settings.

Software for performing BLAST analyses is publicly available through the National Centre for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two polynucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

Mutations may be made to specific bacteriophages by chemical, radiological or other methods well known to those skilled in the art. Mutants with useful characteristics may then be selected by assay of infectious, physical or genetic characteristics, for example the ability to infect previously resistant bacterial strains. Mutation may also be made by homologous recombination methods well known to those skilled in the art. The mutated sequence may comprise deletions, insertions or substitutions, all of which may be constructed by routine techniques. Insertions may include selectable marker genes, for example lacZ, for screening recombinant viruses by, for example, β-galactosidase activity.

Insertions may also include sequences that encode proteins desired for simultaneous administration with the bacteriophages, as described in more detail below. For example, one or more of the bacteriophages in a preparation of the invention may include a sequence encoding an alginase such that the alginase is expressed in an infected bacterial cell.

Bacteriophage-containing products of the invention can be utilized in many situations where conventional antibiotic therapy is problematic. In yet another aspect, the invention provides a method of therapeutic or prophylactic treatment of a bacterial infection characterised by biofilm formation which comprises administering to a human or non-human animal in need thereof one or more bacteriophages capable of targeting bacteria of said infection and simultaneously, separately or sequentially thereto one or more antibiotics. In one embodiment, the bacteriophages employed may be one or more of the deposited bacteriophages noted above capable of targeting *P. aeruginosa* infections. The invention also provides in still further aspect a method of therapeutic or prophylactic treatment of a bacterial infection comprising or consisting of *P. aeruginosa* which comprises administering to a human or non-human animal in need thereof one or more deposited bacteriophages or mutants thereof as discussed above.

In particular, the preparations or strains of the invention may be used to address chronic or antibiotic-resistant infections. Thus, the use of bacteriophage preparations and strains as specified may initially be as a secondary treatment where infection is proving difficult to clear with existing antibiotics, or in combination or rotation where there is a critical need for clearance of infection. Thus, they may be used to complement and supplement antibiotic use, especially, for example, in relation to *P. aeruginosa* infections and other infections characterised by biofilm formation The treated infection may be in a human or animal, for example a dog or a cat. The infection may be, for example, in or on the ear, eye, skin or other topical location. The infection may be systemic. *Pseudomonas aeruginosa* infections that may be treated by the methods of the invention include otitis externa and other ear infections, keratitis and other eye infections, folliculitis, infections of burns and induced graft rejection, wound infections, hospital acquired infections (nosocomial infections) and lung infections, for example in cystic fibrosis. Urinary tract infections and bacteraemias may also be treated.

Specific prophylactic uses of phage according to the invention are: Ocular-inclusion in eye drops, contact lens solutions or additives, embedded or otherwise included into contact lenses, or otherwise formulated for administration into the eye for prevention of *P. aeruginosa* infection.

Aural-inclusion in ear drops, ear plugs, impregnated dressings (e.g cotton wool) devices for implantation (erg. tympanic membrane grafts, bone grafts) or otherwise formulated for administration into the ear for prevention of *P. aeruginosa* infection. Wound dressings, salves, skin grafts and other formulations for the prevention of the infection of body surfaces or of devices within the body with *P. aeruginosa*. Formulation into or for treatment of medical devices, e.g. artificial joints.

The preparations of the invention may further comprise, or may be administered simultaneously, separately or sequentially with further therapeutic agents. For example, treatment with a preparation or strain of the invention may be coordinated with that of another agent relating to the condition being treated. The preparations or strains of the invention may be administered alongside antibiotics to complement or supplement their actions. The preparations or strains of the inventions may be administered alongside agents directed to other aspects of the condition of the patient, for example agents which may reduce inflammation, stimulate or reduce an immune response, relieve pain or otherwise improve the condition of the patient. The preparations or strains of the invention may be administered alongside other agents being used to treat a patient wherein the other agents may lead to an increased risk of bacterial (e.g. *Pseudomonas aeruginosa*) infection. For example, preparations or strains of the invention may be administered to a patient suffering from immunosuppression, such as localized immunosuppression due to treatment with another agent.

In one embodiment, the use of the preparations or strains of the invention to treat a *P. aeruginosa* infection, for example a lung infection, may be supplemented with the administration of an alginase. As explained above, *Pseudomonas* has a tendency to grow in a complex layer known as a biofilm. The biofilm is an assemblage of surface-associated microbial cells that is enclosed in an extracellular polymeric substance (EPS) matrix. Alginate is the major component of the EPS matrix of *P. aeruginosa*. The use of alginase may therefore help to disrupt such *P. aeruginosa* biofilms and potentiate the clearance of infection. Biofilms may be present in a variety of *P. aeruginosa* infections, including infections of the lung and ear. Co-administration of an alginase with a preparation or strain of the invention may be particularly suitable for use in treating such conditions.

The alginase may be included in a composition of the invention together with one or more bacteriophages or may be provided in a separate composition for separate or sequential administration to one or more bacteriophages. The alginase may be provided from a sequence within the genome of a bacteriophage. This may involve the isolation of such bacteriophages from environmental sources or, for example, the genome of a bacteriophage may be engineered by methods known in the art to include such a sequence operably linked to suitable regulatory sequences.

The amount of bacteriophage administered will depend upon the size, location and nature of the area to be treated and the route of administration used. As a successful treatment will lead to multiplication of the bacteriophages and killing of infected bacteria, some treatments, for example those requiring topical infection, may require only a low dose of bacteriophages. This dose is measured in infectious units, usually defined by the ability to form cleared zones or "plaques" on bacterial culture plates. Such units are defined as "plaque forming units" or "pfu". For example, in some cases the dose may be a few hundred infectious units (pfu) or less. A suitable dose may be $10^2$ to $10^8$ pfu, preferably $10^4$ to $10^6$ pfu. In other cases, for example in a systemic or widespread infection, the dose may need to be higher to ensure that the bacteriophages reach all infected areas. In such a case a suitable dose may be in the range of from $10^4$ to $10^{10}$ pfu, preferably from $10^5$ to $10^8$ pfu. When injected, typically 10 μl to 1 ml of bacteriophages in a pharmaceutically acceptable suitable carrier or diluent is administered. For topical administration the volume may be higher, for example 100 μl to 50 ml of the medicament, depending on the size, location and nature of the area to be treated.

Bacteriophage preparations and compositions of the invention may be administered to the human or animal patient topically, systemically, orally, or by some other means suitable for delivering an effective dose to the site of the infection to be treated. Bacteriophage administration will be in such a way that the bacteriophage can be incorporated into bacteria at the site of infection. The routes of administration and dosages described are intended only as a guide since a skilled practitioner will be able to determine the optimum route of administration and dosage for any particular patient and condition.

As indicated above, the invention also extends to non-therapeutic methods of removing, reducing or preventing bacterial contamination characterised by biofilm formation. This in yet another aspect, the invention provides such a method comprising applying to the site or prospective site of such contamination one or more bacteriophages capable of targeting appropriate bacteria and simultaneously, separately or sequentially thereto one or more antibiotics or antiseptics. Such a method may, for example, be applied to P. aeruginosa contamination in which case one or more of the above-noted deposited bacteriophages may again be employed or a mutant thereof. One or more of the same bacteriophages may also be employed non-therapeutically alone to target bacterial contamination comprising or consisting of P. aeruginosa. Such methods may be applied for the treatment of a variety surfaces in both medical and non-medical contexts, e.g. contact lenses, surfaces of devices to be implanted into the body, pipes, ducts and other surfaces where bacterial infections can become established.

Preparations and strains of the invention may also be used in in vitro diagnostic methods to detect the presence of Pseudomonas aeruginosa. Such methods may comprise the steps of contacting a test sample with one or bacteriophages capable of targeting P. aeruginosa as discussed above and determining whether any of the bacteriophages thus added are capable of killing bacteria in the test sample. Preferably, the test sample will be cultured prior to contact with the preparation or strain, for example under conditions suitable to allow growth of any bacteria of the target species that are present. Suitable culture conditions are known in the art, and will depend upon the specific bacterial target species.

A panel of bacteriophages of the invention capable of targeting P. aeruginosa is particularly useful for such methods because it will detect a broad spectrum of bacterial strains or isolates. A single bacteriophage from a preparation of the invention may detect only a small proportion of strains or isolates of a particular bacterial species, and will therefore typically offer a very high false negative rate simply because of this high specificity. However, the use of a preparation of the invention, comprising two or more such bacteriophages, will allow detection of a broad spectrum of strains within a target bacterial species.

In one embodiment, the test sample may be cultured on a solid growth medium, such as on an agar plate. The sample is preferably cultured on said medium for a sufficient time and under suitable conditions for any target bacteria present in the sample to multiply on the surface of the plate. By contacting the surface of the plate with a preparation or strain of the invention, it can be determined whether any of the bacteriophages thus added are capable of infecting and killing the bacteria. The bacteriophage-infected medium may be maintained under suitable conditions for bacteriophage infection and replication, such that the bacteriophages have an opportunity to infect any target P. aeruginosa cells on the plate. This will lead to the development of clear patches (plaques) where bacterial death has occurred, and will indicate that the test sample contained the target bacterial species.

In an alternative embodiment, the test sample may be maintained in a liquid medium. Again, it may be cultured under conditions suitable for bacterial growth. Following the addition of a preparation or strain of the invention, the medium may be maintained for a further period to allow the bacteriophages to infect any target bacteria present. This will lead to a loss of turbidity in the medium when bacterial death occurs, and this will indicate that the test sample contained the target bacterial species.

The test sample may be any sample where the presence of the target bacterial species is suspected. The test sample may be from an environmental or biological source. Such a test sample may be from, or derived from, a fluid or tissue sample obtained from the patient. The sample may be obtained from the location of an infection. In the case of a topical infection, the sample may be obtained by taking a swab from the infected region. The detection method of the invention may be used to determine particular strains of P. aeruginosa responsible for the infection.

An infection capable of being identified using a preparation or strain of the invention will normally be treatable using the same preparation or strain. That is, if the bacteriophages in a preparation of the invention are capable of killing bacteria obtained from the infected area in vitro, they should also be capable of killing the same bacteria in situ at the site of infection.

The detection method of the invention may therefore also be used to identify a suitable preparation or strain of the invention for use in treatment. The detection method of the invention may also be used to identify single bacteriophages that are suitable for use in such treatment individually, rather than in combination. That is, by using different bacteriophages or combinations of bacteriophages in the detection methods of the invention, the bacteriophage(s) with the greatest virulence towards the bacterial strain of the specific infection may be selected for use in treatment. Preferably, a combination of two or more bacteriophages having such activity is selected for use in treatment.

The present invention also includes the identification and use of bacterial "count strains" for the deposited bacteriophages noted above. Such bacterial strains are defined as strains of the target (or a related) bacterium which support the growth of one bacteriophage from the specified group while only permitting limited growth of all other bacteriophage components of the group. These count strains may then be used to assess titres of the bacteriophage stocks.

The preparations of the invention comprise at least two bacteriophages. Across a spectrum of bacterial strains, the growth of any one bacteriophage will be supported with varying efficiency (or not at all). Consequently, titres obtained by assaying across a range of bacterial strains will differ substantially. In order to provide a means of determining/standardising the therapeutic dose to be administered to each patient, 'count' bacterial strains may be used. The principle of this approach is that the growth of each bacteriophage is only supported at a usable level by one of the range of bacterial strains. A count strain can thus be selected for each of the bacteriophages in a mixture which supports the growth of one of the bacteriophages but does not support the growth, or only supports a low level of growth, of the other bacteriophages in the mixture. Titres of each bacteriophage constituent of the mixture may be calculated based on the growth possible on each of the individual count strains.

For example, a suitable count strain may allow at least 1000 times more, at least 1500 times more, at least 2000 times more growth, or greater, of one bacteriophage compared to the other bacteriophages being used in a mixture of bacteriophages.

The differential growth may be assessed, for example by titrating plaque formation on the bacteria when grown on solid growth medium by the bacteriophages at a range of concentrations. Alternatively, the differential growth may be assessed by looking at the size and nature of the plaques so formed. For example, in one embodiment, the count strain may allow at least 1000 times more plaque formation by one bacteriophage than other bacteriophages. Such a bacterium would form a count strain for that bacteriophage. For example, as shown in FIG. 2, a suitable growth strain for BC-BP-03 may show significant plaque formation following infection with BC-BP-03 at a 1,000,000-fold dilution, but little or no plaque formation when infected with other bacteriophages (here BC-BP-01, BC-BP-02 and BC-BP-04) at a 10-fold dilution (100,000 times higher concentration).

Such a count strain may also be used as a propagation strain for production of bacteriophage for use in the compositions of the invention. For example, a composition of the invention may be formed by combining the required count strains in the appropriate quantities. The count strains may therefore have a therapeutic use themselves as a source of bacteriophages.

This technique also enables the replication of each bacteriophage in a therapeutic composition to be monitored individually in a clinical context. Count strains specific for a particular bacteriophage may be used to identify the presence of that bacteriophage in particular, for example in preparations intended for therapeutic use or in tissue samples obtained during or following such therapeutic use. It is anticipated that this method will allow therapeutic bacteriophages to be distinguished from any extraneous bacteriophages that might exist in the strain with which the patient is infected, and would also allow the determination of which bacteriophages in the administered therapeutic mixture are active against that patient's bacterial infection. The 'count' bacterial strains can be used to 'type' any extraneous bacteriophage prior to administration of the bacteriophage therapy. The presence of the required bacteriophages in a composition or medicament may therefore be confirmed prior to treatment and the presence of the bacteriophages at the treatment site may be monitored during and after treatment. This information may be used by the medical practitioner to monitor and adjust the treatment regimen.

The following examples illustrate the invention.

EXAMPLES

I. Initial Selection of Bacteriophages Active Against *Pseudomonas aeruginosa*

(a) Isolation of Bacteriophages Active Against *Pseudomonas aeruginosa*:
(i) $3 \times 10^9$ colony forming units (cfu) of appropriate *Pseudomonas aeruginosa* strain cultured with settled sewage and nutrient broth (total volume 200 ml).
(ii) Suspension incubated at 37° C. for 24 hours.
(iii) 1 ml aliquot removed and filtered through 0.45 µm syringe-top filter.
(iv) Filtered lysate cultured with the same *Pseudomonas aeruginosa* strain used in step (i), and assessed for presence of bacteriophage (see below)
(v) Nutrient agar plates incubated at 37° C. for 24 hours.
(vi) Single plaque 'picked' using sterile 1 mm diameter wire and used to inoculate 3 ml of growth media (the constituents of this media varied between extractions) containing $5 \times 10^6$ cfu/ml of the *Pseudomonas aeruginosa* strain used in step (i).
(vii) Suspension incubated at 37° C. until lysis of bacteria complete (this typically takes between 5-8 hours) and is assessed visually. The visual assessment is facilitated by comparing the turbidity of the bacteriophage-containing bacterial suspension with that of a control suspension. Control suspensions do not receive bacteriophage, yet are similar in every other respect.
(viii) Lysate filtered through 0.1 µm syringe-top filter.
(xi) Lysate adjusted to constitute 2% v/v glycerol, aliquotted into vials and stored at −80° C.
(xii) Titres assessed by co-culturing with appropriate bacterial strain (see below)

(b) Preparation of Master Seeds:
Master seed stocks are established for all bacteriophages as follows:
(i) Primary bacteriophage preparations were co-cultured with appropriate *Pseudomonas aeruginosa* propagating strain on agar plates (see below)
(ii) Single plaques 'picked' using sterile 1 mm diameter wire and used to inoculate 4 ml of Vegetable Peptone Broth containing $5 \times 10^6$ colony forming units (cfu)/ml of the *Pseudomonas aeruginosa* strain used in step (i).
(iii) Suspension incubated at 37° C. until lysis of bacteria complete (this typically takes between 5-8 hours) and is assessed visually. The visual assessment is facilitated by comparing the turbidity of the bacteriophage-containing bacterial suspension with that of a control suspension. Control suspensions do not receive bacteriophage, but are similar in every other respect.
(iv) Lysate filtered through 0.1 µm syringe-top filter.
(v) Master stock adjusted to constitute 2% v/v glycerol, aliquotted into vials and stored at −80° C.
(vi) Titres assessed by co-culturing with appropriate bacterial strain (see below)

(c) Assessment of Titres of Individual Bacteriophages Within a Mixed Population: Bacteriophage vs *Pseudomonas aeruginosa* 'Count' Bacterial Strains
(i) Each bacteriophage (individual suspension) was assayed in duplicate on all count strains. The Master seeds were used.
(ii) Titres were calculated for each bacteriophage on each 'count' bacterial strain.
(iii) Steps (i)-to-(ii) were repeated on two further occasions.
(iv) On the final occasion the mixed bacteriophage suspension containing equal proportions of the 6 individual bacteriophage preparations was assayed in duplicate on all 'count' bacterial strains.
(v) Titres for bacteriophage mix on each 'count' bacterial strain were calculated All three sets of experiments yielded comparable results, which are detailed in Table 1, along with an averaged result TABLE 1a Experiment #1 - Bacteriophage vs 'count' bacterial strains
Titre (pfu/ml) (Titres presented are means of duplicate readings)

| Bacteriophage | P. aeruginosa strain | | | | | |
|---|---|---|---|---|---|---|
| | Count 06 | Count 02 | Count 03 | Count 01 | Count 04 | Count 05 |
| BC-BP-06 | $5 \times 10^9$ | — | — | — | — | — |
| BC-BP-04 | — | — | Barely discernible inhibition. No plaques | — | $1.22 \times 10^8$ | — |
| BC-BP-02 | — | $2 \times 10^8$ | Barely discernible inhibition. No plaques | — | — | — |
| BC-BP-05 | — | — | — | — | — | $2.3 \times 10^9$ |
| BC-BP-01 | — | — | $6 \times 10^2$ | $2.84 \times 10^8$ | — | 'Turbulences' observed at $10^{-1}$ and $10^{-2}$ Dilutes out |
| BC-BP-03 | — | — | $3.1 \times 10^8$ | $2.2 \times 10^3$ | — | — |

TABLE 1b

Bacteriophage vs cross-reacting 'count' bacterial strains;
difference in titres (experiment #1)
Titer (pfu/ml) (Titres presented are means of duplicate readings)

| | P. aeruginosa strain | | |
|---|---|---|---|
| Bacteriophage | Count 03 | Count 01 | Fold difference |
| BC-BP-01 | $6 \times 10^2$ | $2.84 \times 10^8$ | $4.73 \times 10^5$ |
| BC-BP-03 | $3.1 \times 10^8$ | $2.2 \times 10^3$ | $1.4 \times 10^5$ |

TABLE 1c

Experiment # 2 - Bacteriophage vs 'count' bacterial strains
Titre (pfu/ml) (Titres presented are means of duplicate readings)

| Bacteriophage | P. aeruginosa strain | | | | | |
|---|---|---|---|---|---|---|
| | Count 06 | Count 02 | Count 03 | Count 01 | Count 04 | Count 05 |
| BC-BP-06 | $4.8 \times 10^9$ | — | — | — | — | — |
| BC-BP-04 | — | — | Barely discernible inhibition. No plaques | — | $1.22 \times 10^8$ | — |
| BC-BP-02 | — | $7.5 \times 10^8$ | Barely discernible inhibition. No plaques | — | — | — |
| BC-BP-05 | — | — | — | — | — | $1.58 \times 10^9$ |
| BC-BP-01 | — | — | $3.5 \times 10^2$ | $8.1 \times 10^7$ (poor duplicates) | — | 'Turbulences' observed at $10^{-1}$ and $10^{-2}$ Dilutes out |
| BC-BP-03 | — | — | $2.65 \times 10^8$ | $7 \times 10^2$ | — | — |

TABLE 1d

Bacteriophage vs cross-reacting 'count' bacterial strains; difference in titers (experiment #2) Titer (pfu/ml) (Titres presented are means of duplicate readings)

| Bacteriophage | *P. aeruginosa* strain Count 03 | Count 01 | Fold difference |
|---|---|---|---|
| BC-BP-01 | $3.5 \times 10^2$ | $\mathbf{8.1 \times 10^7}$ | $2.3 \times 10^5$ |
| BC-BP-03 | $\mathbf{2.65 \times 10^8}$ | $7 \times 10^2$ | $3.8 \times 10^5$ |

TABLE 1e

Experiment #3 - Bacteriophage vs 'count' bacterial strains; individual and mixed.
Titre (pfu/ml) (Titres presented are means of duplicate readings) Outcome of experiments where the 6 bacteriophages are mixed before assaying shown in bold text

| Bacteriophage | *P. aeruginosa* strain Count 06 | Count 02 | Count 03 | Count 01 | Count 04 | Count 05 |
|---|---|---|---|---|---|---|
| BC-BP-06 | $\mathbf{6.36 \times 10^9}$<br>$5.8 \times 10^9$ | — | — | — | — | — |
| BC-BP-04 | — | — | Barely discernible inhibition. No plaques | — | $\mathbf{4.62 \times 10^8}$<br>$9.6 \times 10^8$ | — |
| BC-BP-02 | — | $\mathbf{1.17 \times 10^9}$<br>$7.5 \times 10^8$ | Barely discernible inhibition. No plaques | — | — | — |
| BC-BP-05 | — | — | — | — | — | $\mathbf{1.53 \times 10^9}$<br>$1.4 \times 10^9$ |
| BC-BP-01 | — | — | $1 \times 10^2$ | $\mathbf{2.61 \times 10^8}$<br>$3.3 \times 10^8$ | — | 'Turbulences' observed at $10^{-1}$ and $10^{-2}$ Dilutes out |
| BC-BP-03 | — | — | $\mathbf{3.69 \times 10^8}$<br>$3.35 \times 10^8$ | $7.5 \times 10^2$ | — | — |

TABLE 1f

Bacteriophage vs cross-reacting 'count' bacterial strains; difference in titres (experiment #3) Titre (pfu/ml) (Titres presented are means of duplicate readings)

| Bacteriophage | *P. aeruginosa* Strain Count 03 | Count 01 | Fold difference |
|---|---|---|---|
| BC-BP-01 | $1 \times 10^2$ | $\mathbf{3.3 \times 10^8}$ | $3.3 \times 10^6$ |
| BC-BP-03 | $\mathbf{3.35 \times 10^8}$ | $7.5 \times 10^2$ | $4.5 \times 10^5$ |

TABLE 1g

Bacteriophage vs 'count' bacterial strains;
mean results of experiments #1, #2 and #3
Titre (pfu/ml) (Titres presented are means of duplicate readings
in experiments #1, #2 and #3)

| | *P. aeruginosa* strain | | | | | |
|---|---|---|---|---|---|---|
| Bacteriophage | Count 06 | Count 02 | Count 03 | Count 01 | Count 04 | Count 05 |
| BC-BP-06 | $5.2 \times 10^9$ | — | — | — | — | — |
| BC-BP-04 | — | — | Barely discernible inhibition. No plaques | — | $4.8 \times 10^8$ | — |
| BC-BP-02 | — | $5.3 \times 10^8$ | Barely discernible inhibition. No plaques | — | — | — |
| BC-BP-05 | — | — | — | — | — | $1.8 \times 10^9$ |
| BC-BP-01 | — | — | $3.5 \times 10^2$ | $2.3 \times 10^8$ | — | 'Turbulences' observed at $10^{-1}$ and $10^{-2}$ Dilutes out |
| BC-BP-03 | — | — | $3 \times 10^8$ | $1.2 \times 10^3$ | — | — |

TABLE 1h

Bacteriophage vs cross-reacting 'count' bacterial strains;
difference in titres. Means of experiments #1, #2 and
3 Titre (pfu/ml) (Titres presented are means of duplicate
readings in experiments #1, #2 and #3)

| | *P. aeruginosa* strain | | |
|---|---|---|---|
| Bacteriophage | Count 03 | Count 01 | Fold difference |
| BC-BP-01 | $3.5 \times 10^2$ | $2.3 \times 10^8$ | $6.6 \times 10^5$ |
| BC-BP-03 | $3 \times 10^8$ | $1.2 \times 10^3$ | $2.5 \times 10^5$ |

(d) Preparation of Purified Bacteriophage Suspensions:

Bacteriophages are prepared for use from master suspensions as follows:

(i) 30 ml suspensions of appropriate growth strains of *Pseudomonas aeruginosa* in Vegetable Peptone Broth inoculated with master seeds of the appropriate bacteriophage at a multiplicity of infection of 0.1.

(ii) Suspension incubated at 37° C. until lysis of bacteria complete (this typically takes between 5-8 hours) and is assessed visually. The visual assessment is facilitated by comparing the turbidity of the bacteriophage-containing bacterial suspension with that of a control suspension. Control suspensions do not receive bacteriophage, but are similar in every other respect.

(iii) Sub-master seeds filtered through 0.45 µm then 0.1 µm syringe-top filters.

(iv) 27 ml of the sub-master seeds carefully over-layed onto 5 ml of a 10% w/v sucrose 'cushion', in 36 ml polypropylene centrifuge tubes. The purpose of the sucrose 'cushion' is to prevent the sedimentation of endotoxins, while allowing the virus particles to pellet at the bottom of the tube.

(v) All centrifuge tubes and buckets thoroughly cleaned and then autoclaved at 121° C. prior to use.

(vi) Tubes spun at 23,500 rpm at 4° C. for 3 hours in a Beckman ultra-centrifuge (vii) Supernatant fractions removed and the pellets drained. Pellets then resuspended in 1 ml PBS+10% v/v glycerol and filtered through 0.2 µm syringe-top filters.

(vi) Titres assessed by co-culturing with appropriate bacterial strain (see below)

This material can be used in vivo, subject to sterility controls:

(e) Sterility

The final product was tested for sterility as follows:

(i) Three 0.6 ml aliquots of final therapeutic product randomly selected (ii) Each aliquot spread out on nutrient agar plate (permissive for growth of a range of bacterial species including *Pseudomonas*) using sterile wire loop (iii) Plates incubated at 37° C. for 48 hours (iv) Plates checked for presence of bacterial colonies (Such Tests on the Material as Prepared Showed No Bacterial Growth)

(f) Assessment of Efficacy:

For the bacteriophage product designed to combat *Pseudomonas aeruginosa* strains which cause canine otitis externa, the development of the product entailed selection of appropriate bacteriophages to fulfill this role. This was achieved by co-culturing a range of 22 bacteriophages with 100 clinical *Pseudomonas aeruginosa* isolates derived from canine otitis externa infections as indicated below. It was found that 90% of these strains were susceptible to at least one of the 6 of the candidate bacteriophages BC-BP-01 to BC-BP-06 (FIG. 1) from the initial panel of 22 strains. These 6 bacteriophages were progressed into clinical trials on the basis that this in vitro data supported the expectation that the product will be clinically effective in vivo.

Method (i) Bacteriophage preparation diluted in PBS in a 10-fold dilution series at room temperature.

(ii) 100 µl of appropriate dilution(s) added to 2.5 ml molten agar at 46° C. containing $5 \times 10^6$ cfu of relevant bacteria.

(iii) Molten agar suspensions poured onto nutrient agar plates and allowed to set at room temperature.

(iv) Plates transferred to 37° C. and incubated for 24 hours.

(v) Plaques counted and numbers used to calculate titre in pfu/ml. One is aiming to count the dilution which gives around 100 plaques per plate.

(g) Assessment of Safety:

A veterinary clinical trial was conducted to assess the toxicity of the bacteriophage product. The total duration of the study was 21 days. Six dogs (3 male; 3 female) received the following treatment regimen administered aurally on 3 occasions, at days 0, 3 and 6 of the study:

| Group | Number of animals | Sex | Treatment | Dose Volume Left Ear | Dose Volume Right Ear |
|---|---|---|---|---|---|
| 1 (control) | 2 | 1 Male | 1 Female Diluent | 0.2 ml | 0.2 ml |
| 2 (test) | 4 | 2 Male | 2 Female Bacteriophage | 0.2 ml (10× therapeutic dose) | 0.2 ml (100× therapeutic dose) |

Administration of the treatment was made by drops of liquid suspension into the external ear canal which was then massaged to promote deep penetration.

The following investigations were undertaken during the study:
(i) Microbiological flora at days 0, 3 and 6 (samples taken immediately prior to administration of treatment) were assessed by plating of ear swabs on:
  1) Cetrimide agar, selective for *Pseudomonas* spp
  2) Mannitol salt agar, selective for *Staphylococcus* spp
  3) Sabouraud dextrose agar, selective for yeast and moulds
  4) FP agar, selective for micrococci
  5) Blood agar, nonselective permitting growth of most microorganisms
(ii) Auroscopic veterinary examination daily until day 8 of the study, then every three days until the conclusion of the study
(iii) Core temperature measured daily Throughout the study:
(i) Auroscopic veterinary examination revealed no significant changes in the condition of the ears of dogs in the test group, as compared with baseline recordings and the control group.
(ii) There were no significant changes in the microbiological flora within the ears of test group dogs, as compared with baseline recordings and the control group.
(iii) In the test group, core temperature recordings did not differ significantly from those noted in the control group or at baseline.

II. Assessment of Clinical Efficacy of Selected Bacteriophages (a) Protection of Mice from Lethal Infection with *Pseudomonas aeruginosa*
1. 150,000,000 infectious units (10 $LD_{50}$) of *Pseudomonas aeruginosa* were to injected into the peritoneal cavities of 20 mice
2. Groups of 5 mice were treated with 4 different concentrations of bacteriophage BC-BP-08, administered simultaneously with the bacterial injection.

TABLE 2

Mouse survival after 150,000,000 infectious units (10 $LD_{50}$) of *Pseudomonas aeruginosa* were injected into the peritoneal cavities of 20 mice

| Bacteriophage (infectious units) | Not surviving | Surviving |
|---|---|---|
| 290,000,000 | 0 | 5 |
| 29,000,000 | 4 | 1 |
| 5,800,000 | 5 | 0 |
| 290,000 | 5 | 0 |

(b) Prevention of the Destruction of Pig Skin In Vitro by *Pseudomonas aeruginosa*

Fourteen wound models were made each consisting of four layers of enzyme cleaned, sterilized, freeze dried pig dermis soaked in human plasma. 100,000 cfu of *P. aeruginosa* were placed on the top of each. Seven of the wound models received 1,000,000 infectious units of phage BC-BP-08, the remainder serving as controls. After 18 hours incubation, 7 of 8 of the controls were blindly assessed as decayed, whereas all of the phage treated models were assessed as not decayed. Bacteria could only be detected in three of the treated discs (median count 0; highest value 12,000). Phages were found to have penetrated through to the bottom layer of the model and have replicated in it (median count in models after incubation: 32,000,000; range 14,000,000-20,000,000,000).

(c) Protection of Skin Grafts on Guinea Pigs from Infection with *Pseudomonas aeruginosa*
1. A 0.2 mm thick rectangle of shaved skin (2 cm×1 cm) was excised from the backs of 14 guinea pigs
2. The underlying skin layers were removed to make the wounds comparable to an excised burn
3. 600,000 infectious units of *Pseudomonas aeruginosa* were introduced into the wounds
4. 12,000,000 infectious units of the bacteriophage BC-BP-08 were introduced into the wounds on 7 animals, with no bacteriophage introduced into the wounds of the other 7
5. The skin rectangle was replaced and dressed
6. Graft success was assessed after 5 days

TABLE 3

Protection of skin grafts on guinea pigs from infection with *Pseudomonas aeruginosa*

| | Graft succeeded | Graft failed |
|---|---|---|
| No bacteriophage | 0 | 7 |
| With bacteriophage | 6 | 1 |

(d) Multiplication of Administered *Pseudomonas aeruginosa* Bacteriophages in the External Auditory Canal of a Dog with Otitis Externa The dog, with a history of atopy, had bilateral chronic otitis externa. Swabs of both ears had repeatedly grown *P. aeruginosa* for many months, despite antibiotic therapy. Before phage therapy, the dog had bilateral swollen erythematous external auditory canals, each with a purulent discharge and copious waxy secretions over the surrounding pinna. Swabs taken from each ear at that time grew as *P. aeruginosa* (identified by API 20NE, Biomerieux, France). The isolates from the two ears had differed slightly in their biochemical reactions and in their antibiotic sensitivity patterns. From a phage collection, eight were selected for testing against the strains, because they had previously been identified as exhibiting good lytic activity against a wide range of *P. aeruginosa* strains. Three of the phages displayed good lytic activity against both isolates obtained from the dog. The phages were further tested for how few plaque-forming units would lyse a standard broth culture of the two isolates. BC-BP-04, the phage for which the number of pfu required for lysis was lowest was chosen for in vivo work. The phage concentration in the stock solution had been titrated, with 0.2 ml of a $10^5$ dilution of this solution being applied by syringe to the dog's right external auditory meatus. This volume contained approximately 400 infectious units (plaque forming units, p.f.u.).

Twenty seven hours after phage application, a swab was taken of the detritus within the right ear. It was weighed before and after swabbing and the mass of detritus was determined. Phages were counted in the detritus by plating serial 10 fold dilutions using the agar overlay technique. There were $1.6 \times 10^8$ phages in the 0.032 g of detritus that was present on the swab, so it is likely that the phage multiplied over 1 million fold. This increase was accompanied by a marked clinical improvement of the right ear. There was less inflammation; disappearance of the purulent discharge; and reduced amount of waxy secretions (FIG. 3a). The appearance of the left ear, which had not received phage, remained unchanged (FIG. 3b). In view of the change, 400 pfu of the phage was applied to the left ear, which was followed by considerable clinical improvement 24-48 hours later. Two weeks after the phage application, the dog's ears had deteriorated; and swabs of both were positive for *P. aeruginosa* on culture. Subsequently the condition of the ears repeatedly deteriorated and improved for many months but the owner and veterinarian judged that their condition was better than it had been before phage was administered. Nine months after phage administration both ears completely recovered, and *P. aeruginosa* has not since been isolated from aural swabs. No antibiotics were given to the dog after phage administration as they were not considered necessary.

(e) Use of a *Pseudomonas aeruginosa* Bacteriophage in the Treatment of an Infection of a Human Burn A single case trial was carried out on a 27 year old man with 50% burns. Episodes of healing of the burns alternated with periods of breakdown of the skin. It was noted that the skin on his back and chest were breaking down. At this time the clinicians, who were concerned by the rapid rate of breakdown of the skin, asked if a phage could be found to treat his *P. aeruginosa* infection. A new phage, BC-BP-07, was isolated that was active. Although in vitro testing did not indicate great activity against the strain, time was limited, so it was selected for further work. A purified suspension was made and no evidence of toxicity of which was shown when it was added to cultures of human epidermal cells. Approximately 1000 infectious units (p.f.u.) of BC-BP-07 were applied to each of two filter paper discs of diameter 25 mm. At a dressing change these were placed on areas of the patient known to be colonised with *P aeruginosa*. 48 hours later counts of phage in the discs were $1.2 \times 10^6$ and $4.3 \times 10^4$, increases of 1,200× and 43×. After this the patient's burns were sprayed with the phage. Following this, the patient's condition gradually improved and he survived and eventually all wounds healed over. Whether the phage contributed to the recovery of the patient, who was also given antibiotics, is unknown, but phage did multiply on the burns and demonstrates the bacteriophage multiplying in or on a patient, thus indicating killing of bacteria by the bacteriophage.

Prior to their deposit at NCIMB on 24 Jun. 2003, none of the bacteriophages referred to herein as BC-BP-01 to BC-BP-08 were publicly available, hence any reference to such strains in any publication or other disclosure before that date does not represent enabling prior art.

In the further exemplification provided below, use was made of a combination of the six bacteriophages NCIMB 41174, NCIMB 41175, NCIMB 41176, NCIMB 41177, NCIMB 41178 and NCIMB 41179 (the BioVet-PA composition) which had been found to be active against 90% of the *Pseudomonas aeruginosa* isolates tested from canine ear infections (otitis externa and other ear infections). 0.2 ml of BioVet-PA contained $1 \times 10^5$ infectious units of each of the six bacteriophages as measured against appropriate count strains as described above.

The six individual purified bacteriophage suspensions were diluted in 10% v/v glycerol/PBS to a concentration of approximately $3 \times 10^6$ pfu/ml. This dilution step was based on titres calculated from the samples of the bacteriophage suspensions that had been frozen at $-80°$ C., then thawed and assayed. After dilution, the six therapeutic bacteriophages were mixed together in equal proportions, thus diluting each bacteriophage by a factor of six and bringing the concentration of the individual constituents to $5 \times 10^5$ pfu/ml. This is equivalent to $1 \times 10^5$ pfu of each therapeutic bacteriophage in 0.2 ml diluent. At this point, the final mixed product was aliquoted into 0.6 ml aliquots and stored at $-80°$ C.

III. Trial of a Combined Phage Composition Against Canine Ear Infections

As indicated above, canine ear infections caused by *Pseudomonas aeruginosa* (otitis externa and otitis media) are examples of clinical disease associated with biofilm-based colonization of a body surface. Clinical signs of such infection include pain, irritation (erythema), ulceration and the discharge of increased amounts of material from the ear. This is often purulent in nature and is accompanied by a distinctive odour. The BioVet-PA combined preparation of six bacteriophages noted above was authorized for trial in dogs with such infection by the Veterinary Medicines Directorate of the United Kingdom under Animal Trials Certificate 20505/0001 issued to Biocontrol Limited on 17th Nov. 2003.

Conduct of the Trial

BioVet-PA was stored at $-80°$ C. Immediately prior to administration, the product was thawed and warmed in the hand. 0.2 ml (containing $1 \times 10^5$ infectious units of each of the 6 bacteriophages) was administered drop-wise using a sterile 1 ml capacity syringe into the ear. Ear condition and microbiology was assessed at 2 days post-administration.

The procedure was as follows:

Characterisation (2 to 14 Days Prior to Treatment):
Day 0 Swabs taken from each ear by a veterinary surgeon
  Laboratory tests carried out using these swabs to confirm presence of *P. aeruginosa*.

If *P. aeruginosa* was not detected, the dog was excluded from the trial
Day 1 If *P. aeruginosa* was detected, the isolates were tested for sensitivity to BioVet-PA.

If the *P. aeruginosa* strain(s) with which the dog was infected was not sensitive to BioVet-PA, the dog was excluded from the trial.

Treatment:
Day 0 Ears examined auroscopically to assess their condition.
  Swabs taken from each ear for microbiological analysis.
  Dog's core temperature measured Dog given dose of 0.2 ml BioVet-PA into the ear (treatments administered drop-wise using a sterile 1 ml-capacity syringe, and ear canals then massaged to promote deep penetration).

Day 1 Ears examined to assess their condition.
Swabs taken from each ear for microbiological analysis.
Dog's core temperature measured.

Day 2 Ears examined to assess their condition.
Swabs taken from each ear for microbiological analysis.
Dog's core temperature measured.

Results:

Studies on six dogs with severe, antibiotic-resistant *Pseudomonas aeruginosa* ear infections treated with BioVet-PA showed improvement in clinical symptoms within two days of treatment (FIG. 4) and reductions in bacterial numbers over the same timescale (FIG. 5). Bacteriophage replication was also observed in all dogs (FIG. 6). Analysis of the improvement in clinical symptoms showed this to be significant at the 95% level of confidence by both the t-test and the Wilcoxon matched-pairs test.

IV. Trial of a Combined Phase Composition with Antibiotics Against Canine Ear Infections The BioVet-PA composition plus antibiotics were used against *Pseudomonas aeruginosa* ear infections in dogs that had proved refractory to antibiotic treatment alone.

Case 1

Dog M had a history of bilateral otitis, which had failed to resolve in the right ear despite repeated courses of treatment with antibiotics, including marbofloxacin and gentamicin, which are used to treat *Pseudomonas otitis*. At the start of the phage trial (Jan. 26, 2004), the right ear was infected with both *Pseudomonas aeruginosa* and a group G beta-haemolytic *Streptococcus*. Examination showed erythema, ulceration, and purulent discharge accompanied by odour. Following examination, dog M was treated with BioVet-PA (100,000 infectious units of each of the six bacteriophages in 0.2 ml of diluent).

Analysis following treatment showed that five of the six bacteriophages were replicating. This was accompanied by a fall in the number of *Pseudomonas* bacteria present in the ear and by improvement in clinical symptoms. Eight days after the completion of a two day monitoring period following bacteriophage treatment, dog M was treated with Synulox (amoxicillin and clavanulate) for the accompanying *Streptococcus* infection. This therapy also has some activity against some *Pseudomonas* strains.

Result

Analysis of a swab taken on Mar. 08, 2004 showed no detectable *Pseudomonas*, accompanied by low levels of *Streptococcus*. This demonstrated the efficacy of bacteriophages in resolving bacterial infection in a system characterised by biofilm formation when antibiotics and other chemical agents had previously failed to clear the infection, along with improved results when antibiotics are administered after such treatment.

Case 2

Dog R had a history of bilateral otitis, which had failed to resolve despite treatment with gentamicin, marbofloxacin (used for the treatment of *Pseudomonas otitis*), ampicillin (used for other bacterial infections) and rimadyl (an anti-inflammatory). Dog R was examined on Feb. 16, 2004. At this time, both ears were infected with both *Pseudomonas aeruginosa* and with coliform bacteria. Both ears were producing purulent discharges accompanied by intense odour. Erythema and ulceration were also marked. Following examination, dog R was treated with BioVet-PA (100,000 infectious units of each of the six bacteriophages in 0.2 ml of diluent). Analysis following treatment showed that two of the six bacteriophages were replicating. This was accompanied by a fall in the number of *Pseudomonas* bacteria present in the ear and by improvement in clinical symptoms. Following a four day monitoring period after bacteriophage treatment, dog R was treated with Amoxicillin Clavulanate tablets (for coliform bacteria present in the ear) and Canaural ear drops (containing diethanolamine fusidate, framycetin sulphate, nystatin and prednisolone). *Pseudomonas aeruginosa* present in the ears was known to be partially resistant to aminoglycoside antibiotics such framycetin. The other components of the Canaural formulation are not used against *Pseudomonas* (diethanolamine fusidate is an antibiotic used against other bacterial infections including coliform bacteria, nystatin is an antifungal agent; prednisolone is an anti-inflammatory) Antibiotic sensitivity of the coliform infection was unknown, but a course of ampicillin completed on Jan. 30, 2004 had failed to resolve the infection.

Result

Examination of dog R on Mar. 01, 2004 showed that clinical symptoms had resolved completely in both ears. Erythema and ulceration were absent, discharges were normal and no odour was detected. This demonstrated the efficacy of antibiotic treatment undertaken after application of bacteriophages in resolving the clinical symptoms of infection when antibiotics and other chemical agents had failed to clear the infection.

The invention claimed is:

1. A method of treatment of a bacterial infection characterized by biofilm formation, wherein said bacterial infection comprises *Pseudomonas aeruginosa*, and wherein said method comprises:
   (a) administering to a human or non-human animal in need thereof one or more bacteriophage preparations comprising bacteriophages NCIMB 41174, NCIMB 41175, NCIMB 41176, NCIMB 41177, NCIMB 41178 and NCIMB 41179, wherein said bacteriophages target and kill said *Pseudomonas aeruginosa* present in the biofilm; and
   (b) sequentially administering one or more antibiotics active against a bacterial species present in the biofilm, wherein said one or more antibiotics is administered after the bacteriophages have commenced replication in a targeted *Pseudomonas aeruginosa* present in the biofilm.

2. The method of claim 1, wherein the bacteriophages are employed in the form of a single combined bacteriophage preparation.

3. The method of claim 2, wherein said combined bacteriophage preparation comprises a plurality of bacteriophages capable of infecting the *Pseudomonas aeruginosa*, each member of said plurality of bacteriophages having a different strain specificity.

4. The method of claim 1, wherein said infection is an infection selected from infection of a skin burn or other skin wound, a lung infection, an ocular infection, an ear infection, a urinary infection or infection associated with a medical device or implant.

5. The method of claim 4, wherein said infection is an ear infection.

6. A method of treatment of a bacterial infection characterized by biofilm formation, wherein said bacterial infection comprises *Pseudomonas aeruginosa*, and wherein said method comprises:

(a) administering to a human or non-human animal in need thereof one or more bacteriophage preparations comprising bacteriophages, wherein said one or more bacteriophages target and kill said *Pseudomonas aeruginosa* present in the biofilm; and (b) sequentially administering one or more antibiotics active against a bacterial species present in the biofilm, wherein said one or more antibiotics is administered after the bacteriophages have commenced replication in a targeted *Pseudomonas aeruginosa* present in the biofilm, wherein a panel of bacteriophages is employed consisting of NCIMB 41174, NCIMB 41175, NCIMB 41176, NCIMB 41177, NCIMB 41178, NCIMB 41179, and said panel of bacteriophages is employed in the form of a single combined bacteriophage preparation for use in treating an ear infection.

7. The method of claim 1, wherein administration of said one or more antibiotics is delayed by at least one day after administration of said one or more bacteriophage preparations.

* * * * *

UNITED STATES PATENT AND TRADEMARK OFFICE
CERTIFICATE OF CORRECTION

PATENT NO.         : 7,807,149 B2                                        Page 1 of 1
APPLICATION NO.    : 10/565347
DATED              : October 5, 2010
INVENTOR(S)        : James Soothill It is certified that error appears in the above-identified patent and that said Letters Patent is hereby corrected as shown below:

In the claims:

Col. 29, line 5, please delete "*nosa*present" and insert --*nosa* present--

Signed and Sealed this
Thirtieth Day of August, 2011

David J. Kappos
*Director of the United States Patent and Trademark Office*